United States Patent
Wang et al.

(10) Patent No.: US 11,186,680 B2
(45) Date of Patent: Nov. 30, 2021

(54) METHOD FOR PREPARING BIODEGRADABLE POLYESTER ELASTOMER

(71) Applicant: NATIONAL TSING HUA UNIVERSITY, Hsinchu (TW)

(72) Inventors: Jane Wang, Lexington, MA (US); Ken-Sen Chou, Hsinchu (TW); Sung-Nien Hsu, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 16/857,259

(22) Filed: Apr. 24, 2020

(65) Prior Publication Data

US 2020/0247945 A1 Aug. 6, 2020

Related U.S. Application Data

(63) Continuation-in-part of application No. 16/102,787, filed on Aug. 14, 2018, now abandoned, which is a continuation-in-part of application No. 15/154,263, filed on May 13, 2016, now abandoned.

(30) Foreign Application Priority Data

Dec. 25, 2015 (TW) .................................. 104143780

(51) Int. Cl.
| | | |
|---|---|---|
| *C08G 63/85* | (2006.01) | |
| *C08G 63/20* | (2006.01) | |
| *C08G 63/52* | (2006.01) | |
| *B01J 27/053* | (2006.01) | |
| *A61L 27/58* | (2006.01) | |
| *A61L 27/18* | (2006.01) | |

(52) U.S. Cl.
CPC .............. *C08G 63/85* (2013.01); *A61L 27/18* (2013.01); *A61L 27/58* (2013.01); *B01J 27/053* (2013.01); *C08G 63/20* (2013.01); *C08G 63/52* (2013.01)

(58) Field of Classification Search
CPC .............................. B01J 21/063; B01J 27/053
See application file for complete search history.

(56) References Cited

U.S. PATENT DOCUMENTS

2010/0105858 A1* 4/2010 Oki ........................ C08G 63/85
528/279

FOREIGN PATENT DOCUMENTS

| CN | 101028543 | * | 9/2007 |
| CN | 103846093 | * | 11/2014 |

OTHER PUBLICATIONS

M. Kbodadadi et al "Preparation of Titania based solid strong acid and study of its catalytic activity in esterification of Phthalic anhydride and Sebacic acid", 2005 (Year: 2005).*
Enriquez et al "Synthesis of Solid Acid Catalysts Based on TiO2—SO4 and Pt/ Applied in n-Hexane Isomerization", Open Journal of Metal, 2013, 3, 34-44. (Year: 2013).*
Stumbe et al "Hyperbranched Polyesters Based on Adipic Acid and Glycerol", Macromol. Rapid Commun. 2004, 25, 921-924 (Year: 2004).*
Demetris Kafouris et al "Biosourced Amphiphilic Degradable Elastomers of Poly(glycerol sebacate): Synthesis and Network and Oligomer Characterization", Macromolecules, 2013 (Year: 2013).*

* cited by examiner

*Primary Examiner* — Ling Siu Choi
*Assistant Examiner* — Gennadiy Mesh
(74) *Attorney, Agent, or Firm* — Li & Cai Intellectual Property (USA) Office

(57) ABSTRACT

A method for preparing a biodegradable polyester elastomer includes a following steps comprising: dissolving a predetermined amount of titanium dioxide in an aqueous mixture of sulphuric acid, DI water, and ethanol to form a first solution; refluxing the first solution in a silicone oil bath and a stirring speed of 300-450 rpm at a temperature of 90-100° C. to form a second solution; preparing a solid superacid catalyst by drying, grinding and calcining sulfated titania and using this catalyst to produce a biodegradable polyester elastomer.

5 Claims, 9 Drawing Sheets

METHOD FOR PREPARING BIODEGRADABLE POLYESTER ELASTOMER

CROSS-REFERENCE TO RELATED PATENT APPLICATION

This application is a continuation-in-part of U.S. application Ser. No. 16/102,787, filed on 14 Aug. 2018 and entitled "METHOD FOR PREPARING BIODEGRADABLE POLYESTER ELASTOME", the entire disclosures of which are incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The instant disclosure relates to a method for preparing a biomedical material, and more particularly to a method for preparing a biodegradable polyester elastomer having an excellent biocompatibility and biodegradability and good mechanical properties.

BACKGROUND OF THE DISCLOSURE

In recent years, the incidence of ischaemic vascular diseases has increased year by year due to bad eating habits and aging population. In addition, cerebral, cardiac, or peripheral vascular disease caused by artery ischemia seriously affects human health, and thereby has more readily attracted the attention of doctors and researchers. Methods of clinical treatment for ischaemic diseases include targeting drugs, cavity intervention, vascular bridges, etc. However, these methods have the following problems: (1) the need for secondary surgery due to postoperative vascular occlusion; (2) the lack of biological compatibility and mechanical properties of intervention materials; and (3) the lack of stability and therapeutic effect of drugs. Hence, there is a need for methods of promoting vascularization of ischaemic tissue to effectively recover blood supply.

Vascular tissue engineering is one of the most effective ways to solve the aforementioned problems, and how to choose the best tissue engineering scaffold material is the key point thereof. In general, a suitable tissue engineering scaffold material should have the advantages of high specific surface area, good channel connectivity, high biological compatibility, adjustable degradation rate, good mechanical properties, and environmental benefits of cell culture and tissue growth. A material with high biological compatibility usually means that said material is a low toxicity non-carcinogenic material, and cannot cause any allergic reaction, thrombolysis, tissue multiplication, and infection.

Since tissue engineering scaffold materials with the characteristics of mechanical stimulation and biodegradability are beneficial to vascularization of ischaemic tissue, biodegradable elastomers are widely used in the field of biomedical materials. Biodegradable elastomers can be thermoplastic and thermoset. The thermoplastic elastomer is a block polymer which includes soft segments and hard segments interacting with the soft segments, and the thermoset elastomer is a star-branched polymer. Yadong Wang et al. disclose a melt-polymerization reaction between sebacic and glycerol (1:1 molar ration) for the production of poly (glycerol sebacate) (PGS). However, said melt-polymerization reaction will not only result in bad physical performance, but also take 24 hours or more. There is an urgent need for technologies used to improve the reaction rate and product yields of polymerization of biodegradable elastomers.

SUMMARY OF THE DISCLOSURE

In response to the above-referenced technical inadequacies, the present disclosure provides a method for preparing a biodegradable polyester elastomer in a highly efficient manner. The biodegradable polyester elastomer can be produced within a relatively short period of time and has good comprehensive performance.

In one aspect, the present disclosure provides a method for preparing a biodegradable polyester elastomer, including: dissolving a predetermined amount of titanium dioxide in an aqueous mixture of sulphuric acid, DI water, and ethanol to form a first solution; refluxing the first solution at a temperature of 90-100° C. to form a second solution; drying the second solution to form a catalyst raw material; grinding the catalyst raw material and calcining resulting particles at a temperature of 350-550° C. to form sulfated titania as a solid superacid catalyst; and carrying out an esterification reaction between a diacid having 6 to 12 carbon atoms and glycerol in a molar ratio of 1:1-2 with an effective amount of the sulfated titania under a vacuum pressure of 300-600 mTorr to produce a prepolymer.

In certain embodiments, the effective amount of the sulfated titania is at least 1.5-2 mol % based on the diacid and glycerol.

In certain embodiments, the sulfated titania is a 500° C. calcined sulfated titania catalyst.

In certain embodiments, the first solution is refluxed in a silicone oil bath with a stirring speed of 300-450 rpm.

In certain embodiments, the second solution is dried at a temperature of 90-120° C.

In certain embodiments, the diacid is sebacic acid, maleic acid, or adipic acid.

In certain embodiments, the esterification reaction is carried out at a temperature of 25-150° C.

In certain embodiments, the esterification reaction is carried out at 130-150° C.

In certain embodiments, the esterification reaction is carried out with a stirring speed of 300-400 rpm.

One of the advantages of the instant disclosure is that the method uses sulphuric acid as a solid superacid catalyst to promote the esterification reaction between a specific diacid and glycerol, such that the reaction time can be reduced significantly and the polyester elastomer (i.e., PGS polymer) produced has an excellent biocompatibility and biodegradability and good mechanical properties.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
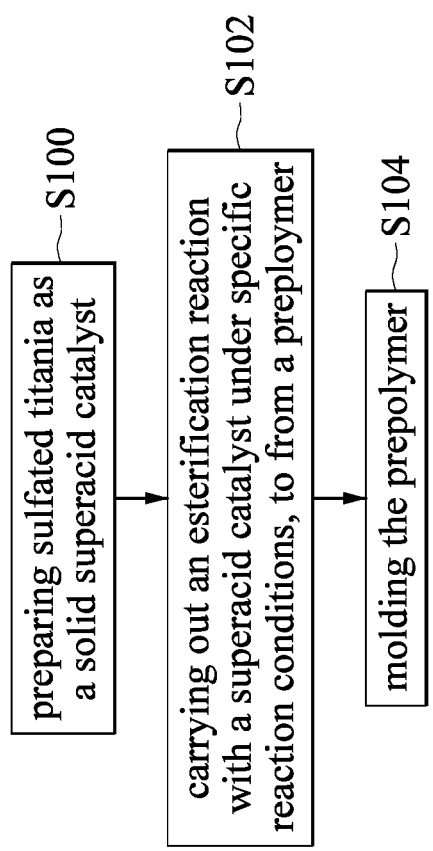
FIG. 1 is a flowchart of a method for preparing a biodegradable polyester elastomer according to one embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Biodegradable elastomers can experience mechanical forces and deformation, and do not appear to affect surrounding tissues during the process of recovery. In addition, biodegradable elastomers have a certain water absorption ratio, high hydrophilicity, and mechanical properties which are similar to proteins. Accordingly, they can be applied in biomedical field to be used as templates for forming tissue engineering scaffold materials. The present disclosure provides a method for preparing a biodegradable polyester elastomer in the presence of a prepared sulfated titania as a solid superacid catalyst under specific reaction conditions (e.g., temperature and pressure). Therefore, the production time of the biodegradable polyester elastomer can be reduced to less than about 60 minutes so as to meet the requirements of large-scale production. In addition, the sulfated titania can be recovered from the prepolymer for reuse.

FIG. 1 is a flowchart of a method for preparing a biodegradable polyester elastomer according to embodiments of the present disclosure. As shown in FIG. 1, the method includes: step S100, preparing sulfated titania as a solid superacid catalyst; step S102, carrying out an esterification reaction with a superacid catalyst under specific reaction conditions to form a prepolymer; and step S103, molding the prepolymer.

It is worth mentioning that the method uses a sulfated titania catalyst ($TiO_2/SO_4^{2-}$) to promote the esterification reaction between acid and alcohol components, preferably between a diacid and glycerol, such that the reaction time can be reduced significantly. The sulfated titania catalyst is a superacid catalyst having a tetragonal crystal structure and exhibiting both Lewis and Bronsted acid properties, such that it is capable of promoting the esterification reaction. The resulting biodegradable polyester elastomer has good comprehensive performance and therefore it can be widely used in biomedical fields as well as industrial fields.

Furthermore, the sulfated titania catalyst has good stability and can be easily regenerated even at a relatively low temperature. In addition, the sulfated titania catalyst can be easily prepared and is very suitable for being used in industrial reactions.

In the step S100, the solid superacid catalyst is prepared by wet impregnation, such that sulfate ions can be uniformly bonded to the surface of titania. More specifically, a predetermined amount of titanium dioxide ($TiO_2$) is dissolved in an aqueous mixture of sulphuric acid ($H_2SO_4$), DI water and ethanol ($C_2H_5OH$) to form a first solution firstly. In the aqueous mixture, the titanium dioxide is present in an amount of 0.125 mole, the sulphuric acid is present in an amount of 0.5 mole, the DI water is present in an amount of 5.5 mole, and the ethanol is present in an amount of 2.17 mole. Next, the first solution is refluxed at a temperature of 90-100° C. and 1 atm to form a second solution. Next, the second solution is dried to form a catalyst raw material. The second solution can be dried at a temperature of 90-120° C. Finally, the catalyst raw material is ground and the resulting particles are calcined at a temperature of 350-550° C. for at least four hours to form a sulfated titania catalyst. The sulfated titania catalyst is represented by the formula (1) or (2), where M represents titanium (Ti).

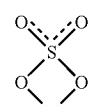

formula (1)

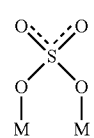

formula (2)

Figure 2:
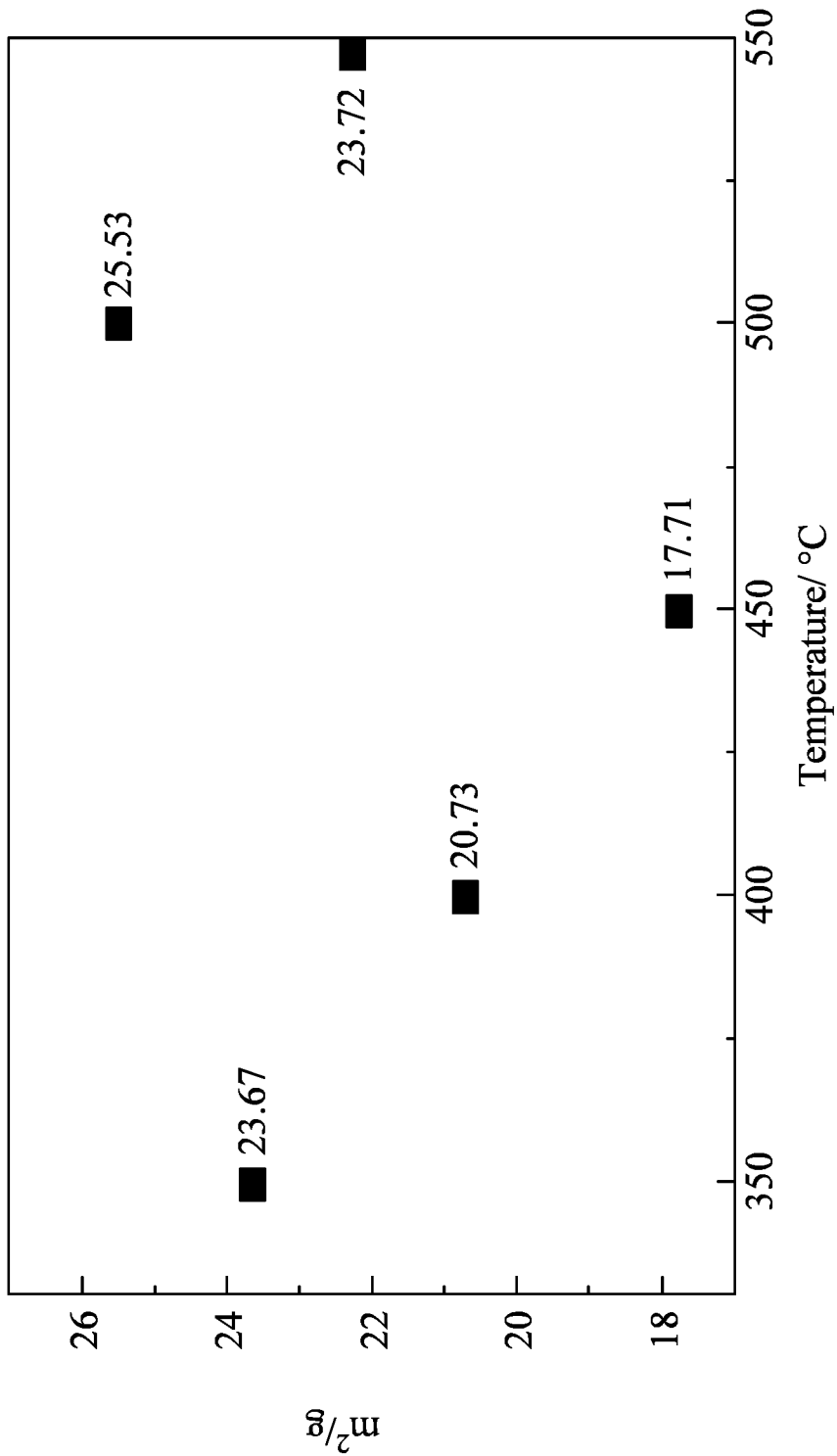
FIG. 2 shows BET (Brunauer-Emmett-Teller) surface areas of sulfated titania resulted from different calcination temperatures.
Figure 3:
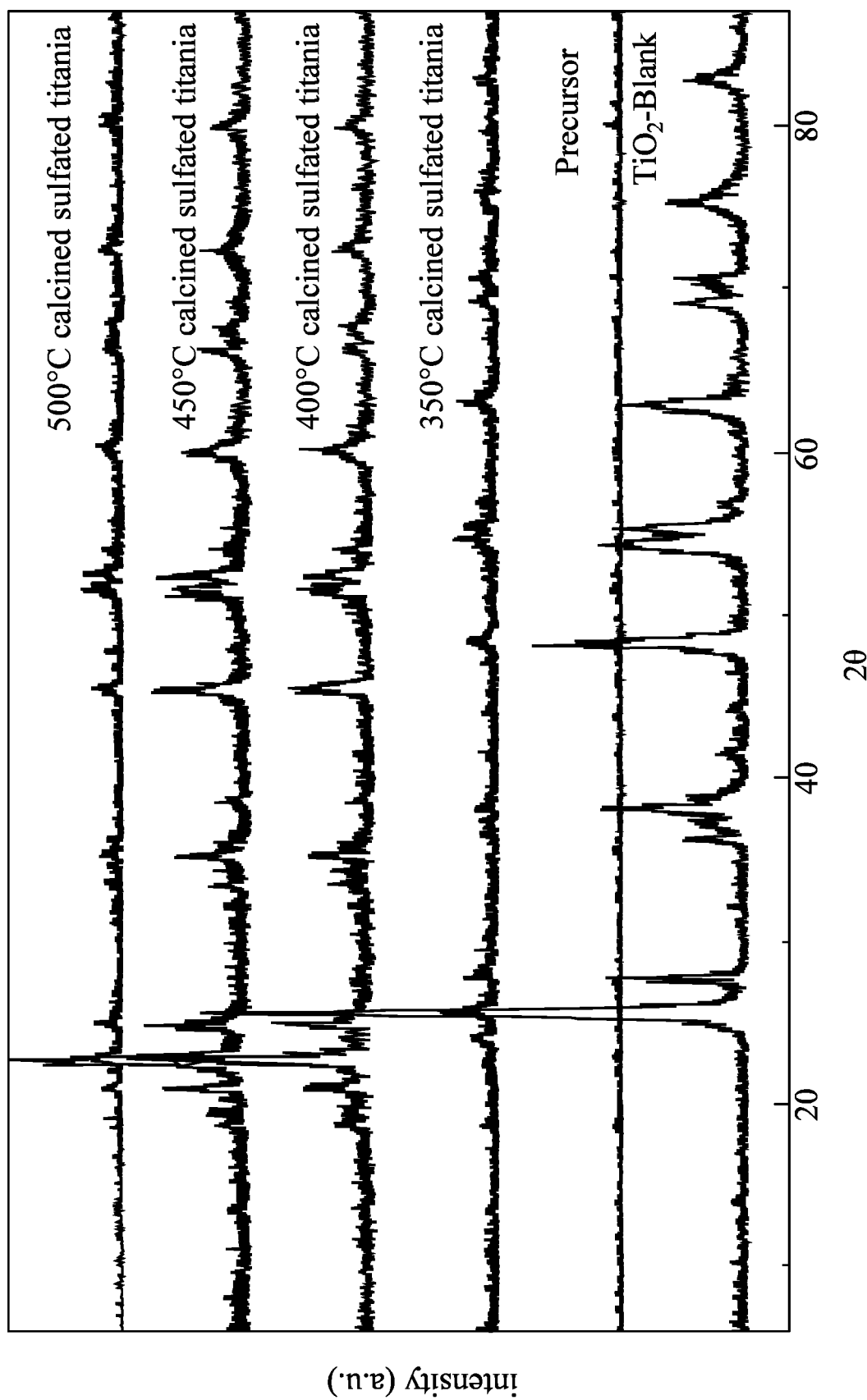
FIG. 3 shows XRD patterns of sulfated titania resulted from different calcination temperatures.
Figure 4:
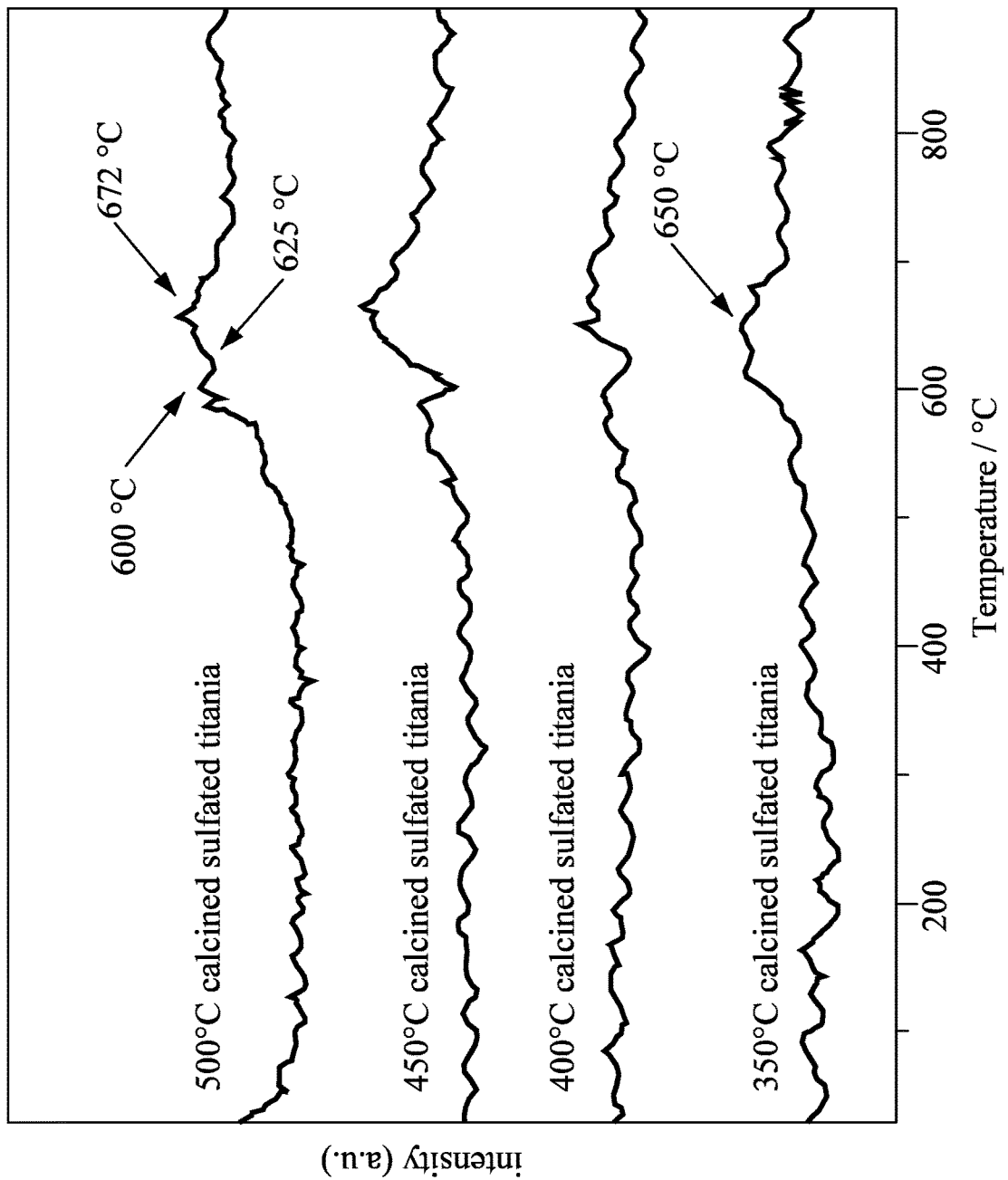
FIG. 4 shows NH3 temperature programmed desorption (NH3-TPD) profiles of sulfated titania resulted from different calcination temperatures.

Reference is now made to FIG. 2 to FIG. 4. FIG. 2 shows BET (Brunauer-Emmett-Teller) surface areas of the sulfated titania catalysts resulted from different calcination temperatures. As shown in FIG. 2, the 500° C. calcined sulfated titania catalyst has a specific surface area of 25.53 m²/g that is the highest surface area. FIG. 3 shows XRD patterns of the sulfated titania catalyst resulted from different calcination temperatures. As shown in FIG. 3, all the sulfated titania catalysts have anatase and rutile phases. FIG. 4 shows NH3 temperature programmed desorption (NH3-TPD) profiles of the sulfated titania catalysts resulted from different calcination temperatures. It is observed that the desorption peak of the 500° C. calcined sulfated titania catalyst shift slightly towards a higher temperature relative to the desorption peaks of the sulfated titania catalysts resulted from other temperatures. This indicates that the average acid strength of the catalyst is slightly increased with an increase in sulfate concentration/sulfur loading. Specifically, compared to the sulfated titania catalyst resulted from other temperatures, the 500° C. calcined sulfated titania catalyst resulted has a greater number of acid sites. Based on the above, the 500° C. calcined sulfated titania catalyst is an optimized superacid catalyst for the esterification reaction.

In the step S102, the esterification reaction can be carried out in a reactor. In the present embodiment, a diacid having 6 to 12 carbon atoms and glycerol are used in the esterification reaction in a molar ratio of 1:1-2. The diacid is preferably sebacic acid, maleic acid, or adipic acid. The reactor can be a batch reactor, but is not limited thereto. In practice, any suitable reactor well known in the art can be used to mix the acid compound and the alcohol compound.

In other embodiments, a polybasic acid having more than 6 carbon atoms and a polyol having 4 to 10 carbon atoms can be used in the esterification reaction. Specific examples of the polybasic acid include suberic acid, azelaic acid, citric acid, phthalic acid, isophthalic acid, trimellitic acid, and 1,2,4,5-pyromellitic acid. Specific examples of the polyhydric alcohol include ethylene glycol, 1,2-propylene glycol, 1,3-propane diol, glycerol, 1,4-butane diol, 1,3-butane diol, 1,6-hexane diol, 1,10-decane diol, diethylene glycol, triethylene glycol, pentaerythritol, and pentaerythritol.

The reaction conditions used for the esterification reaction include a reaction temperature of 25-150° C., preferably 130-150° C., a vacuum pressure of 300-600 mTorrs, and a stirring speed of 300-400 rpm. The sulfated titania catalyst is preferably present in an amount of at least 1.5-2 mol % based on the acid and alcohol components. Accordingly, the reaction time can be reduced significantly. The biodegradable polyester elastomer is preferably a glycerol-sebacic acid (poly(glycerol sebacate)) prepolymer, a glycerol-maleic acid prepolymer, or a glycerol-adipic acid (poly(glycerol adipate)) prepolymer, but it is not limited thereto.

More specifically, the temperature effect on the reaction time reduction is shown below:

TABLE 1

| Prepolymer (Min) | Gel Time (Min) | Reaction Temp. (° C.) |
| --- | --- | --- |
| 90 | 103 | 130 |
| 55 | 73 | 140 |
| 30 | 40 | 150 |

As shown in Table 1, the gelation time and the prepolymer synthesis time of the esterification reaction between sebacic acid and reagent grade glycerol, which is carried out with an effective amount of the sulfated titania catalyst, under a vacuum pressure of 300-600 mTorr and at 150° C., can be decreased to less than about 40 minutes.

TABLE 2

| Prepolymer (Min) | Gel Time (Min) | Reaction Temp. (° C.) |
| --- | --- | --- |
| 100 | 142 | 130 |
| 58 | 83 | 140 |
| 20 | 30 | 150 |

As shown in Table 2, the gelation time and the prepolymer synthesis time of the esterification reaction between sebacic acid and industrial grade glycerol, which is carried out with an effective amount of the sulfated titania catalyst, under a vacuum pressure of 300-600 mTorr and at 150° C., can be decreased to less than about 30 minutes.

TABLE 3

| Prepolymer (Min) | Gel Time (Min) | Reaction Temp. (° C.) |
| --- | --- | --- |
| 100 | 125 | 130 |
| 55 | 73 | 140 |
| 48 | 55 | 150 |

As shown in Table 3, the gelation time and the prepolymer synthesis time of the esterification reaction between sebacic acid and USP grade glycerol, which is carried out with an effective amount of the sulfated titania catalyst, under a vacuum pressure of 300-600 mTorr and at 150° C., can be decreased to less than about 55 minutes.

Figure 5:
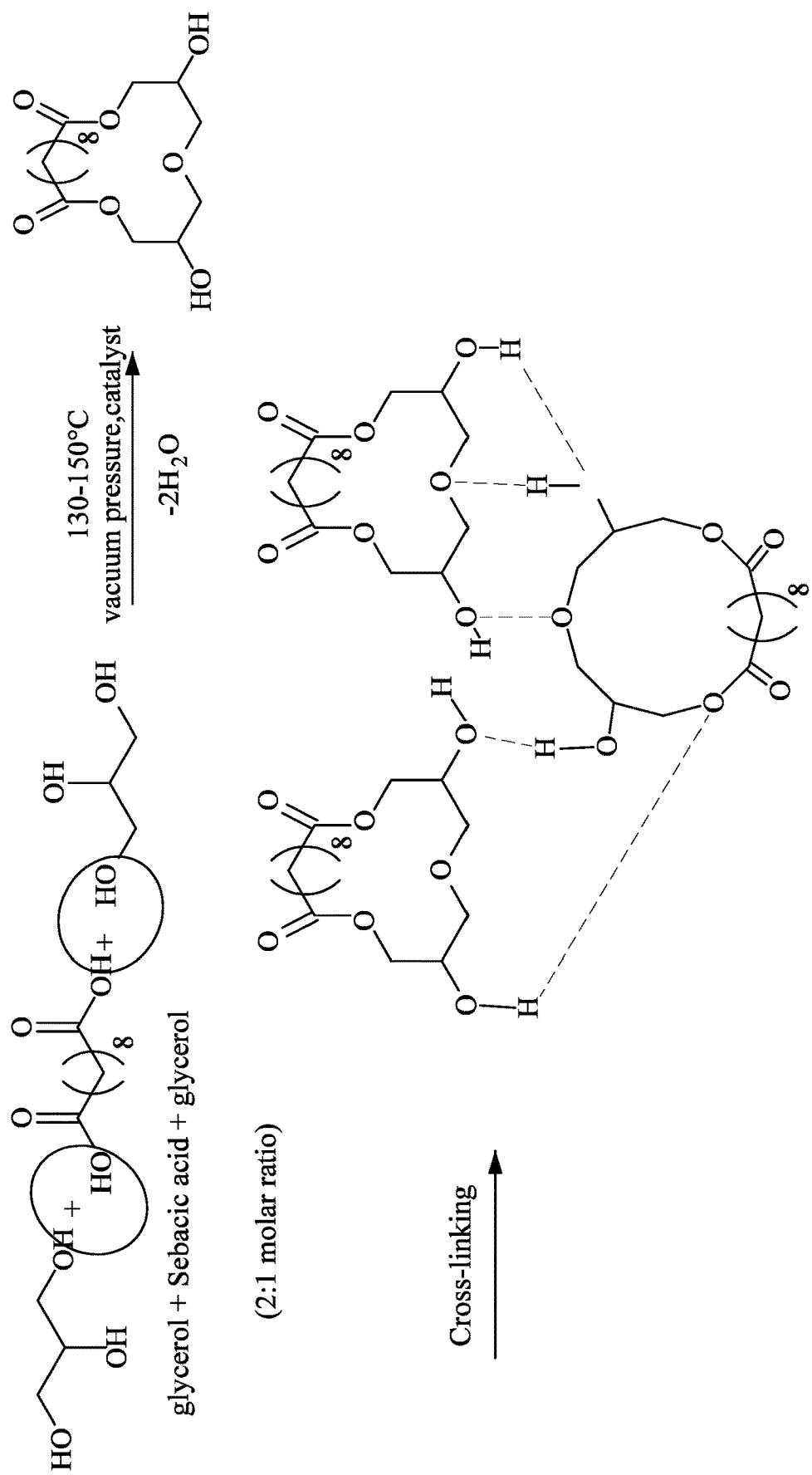
FIG. 5 is a schematic view illustrating an esterification reaction between an acid compound and an alcohol compound without a superacid catalyst.
Figure 6A:
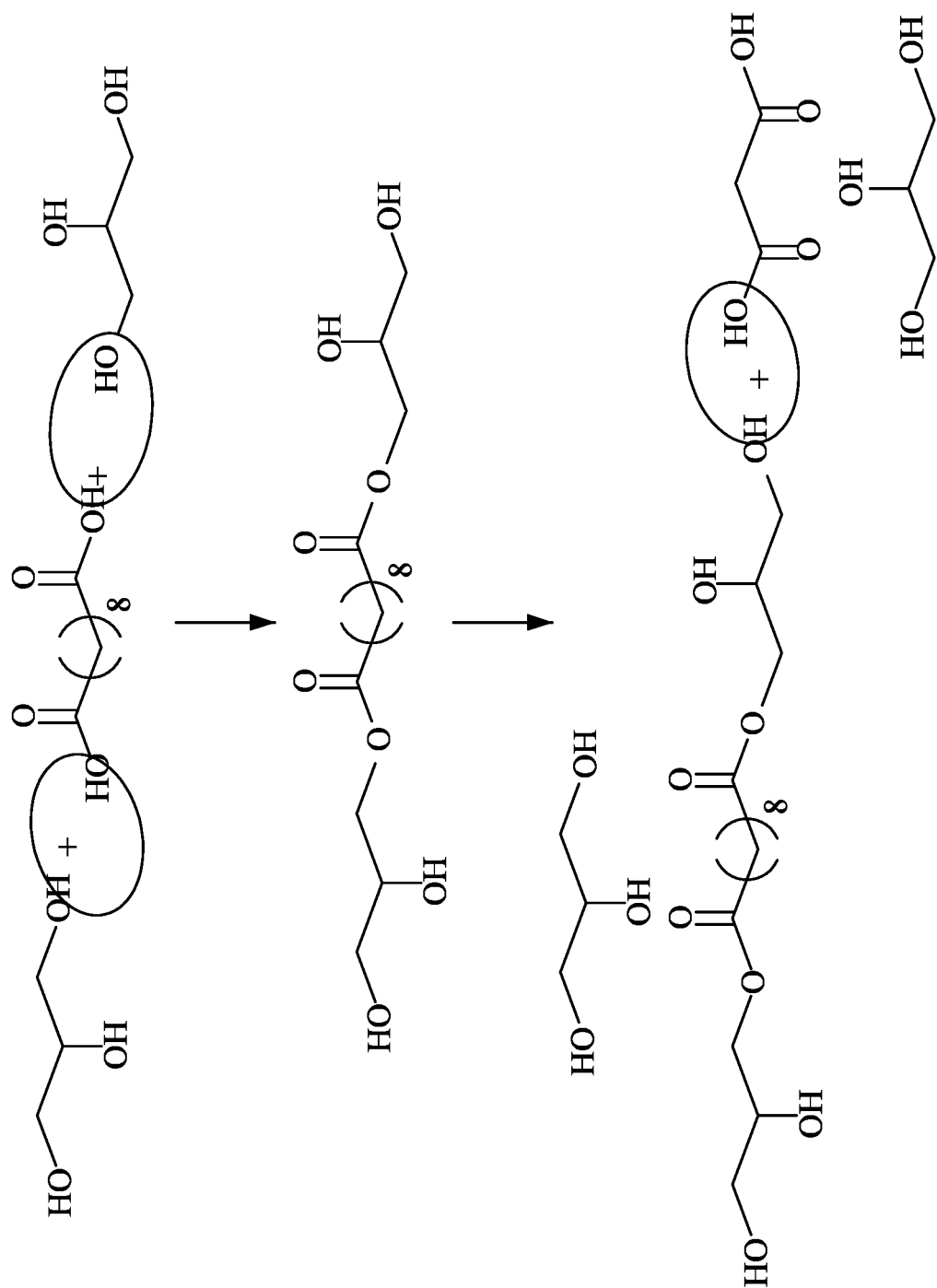
FIGS. 6A and 6B are schematic views illustrating another esterification reaction between the acid compound and the alcohol compound with the solid superacid catalyst.
Figure 6B:
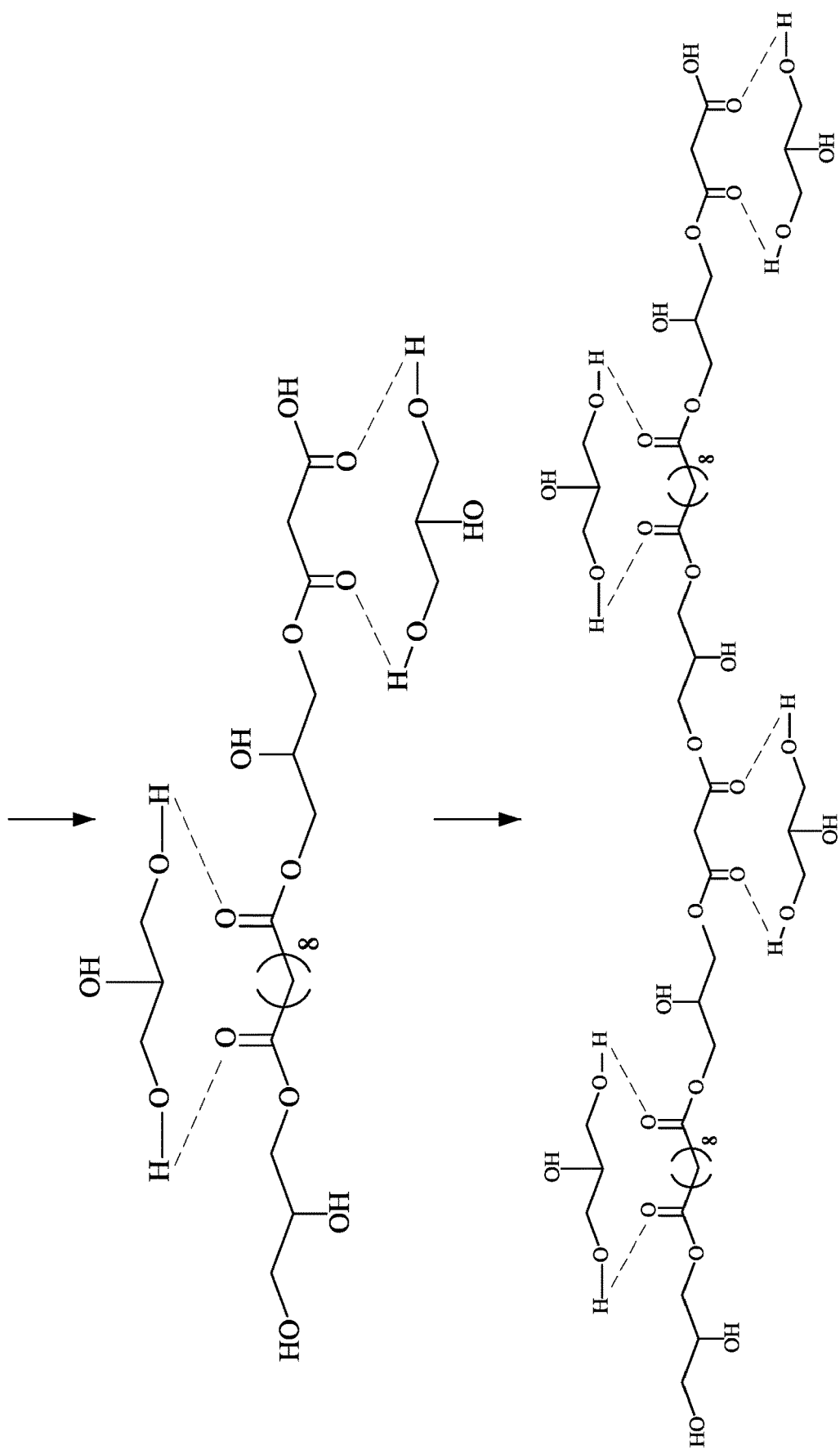

Reference is made to FIGS. 5, 6A, and 6B. The following will describe two different reaction mechanisms associated with the esterification reaction between sebacic acid and glycerol with and without the sulfated titania catalyst. As shown in FIG. 5, an esterification reaction between sebacic acid and glycerol in a molar ratio of 1:2 is carried out with the sulfated titania catalyst and at a temperature of 130-150° C. In the formation of poly(glycerol sebacate) (PGS), two OH-radicals respectively separate from two ends of the main chain of sebacic acid and a hydrogen radical separates from one end of the main chain of each glycerol, and subsequently, the main chain of sebacic acid is linked with the two main chains of glycerol. In the case of not adding the sulfated titania catalyst, a plurality of PGS are crosslinked together to form ring-shaped products.

As shown in FIGS. 6A and 6B, another esterification reaction between sebacic acid and an excess amount of glycerol is carried out with the sulfated titania catalyst and at a temperature of 130-150° C. In the formation of poly (glycerol sebacate) (PGS), two OH-radicals respectively separate from two ends of the main chain of sebacic acid and a hydrogen radical separates from one end of the main chain of each glycerol, and subsequently, the main chain of sebacic acid is linked with the two main chains of glycerol. It should be noted that, in the presence of sulfated titania, hydrogen radicals would continuously separate from one end or two ends to be linked with main chains of the plurality of PGS, so as to form a plurality of linear semi-finished products. According to different active sites of the sulfated titania catalyst, different types of prepolymer as shown in 6A and 6B are synthesized. In the cross-linking reaction, the three-dimensional structure is formed from a number of linear and planar structures to form the elastomer.

Figure 7:
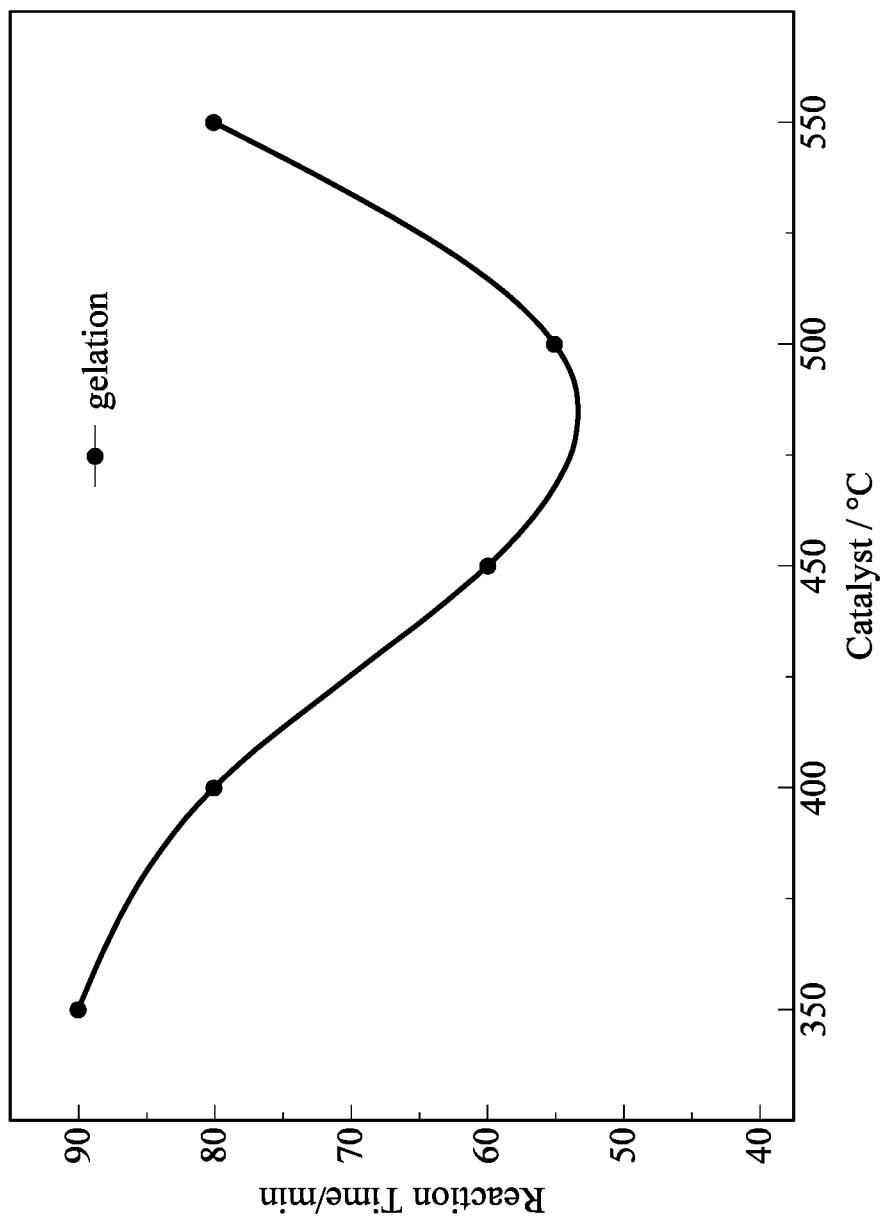
FIGS. 7 and 8 are curve diagrams showing reaction times based on different catalysts prepared at different calcination temperatures.
Figure 8:
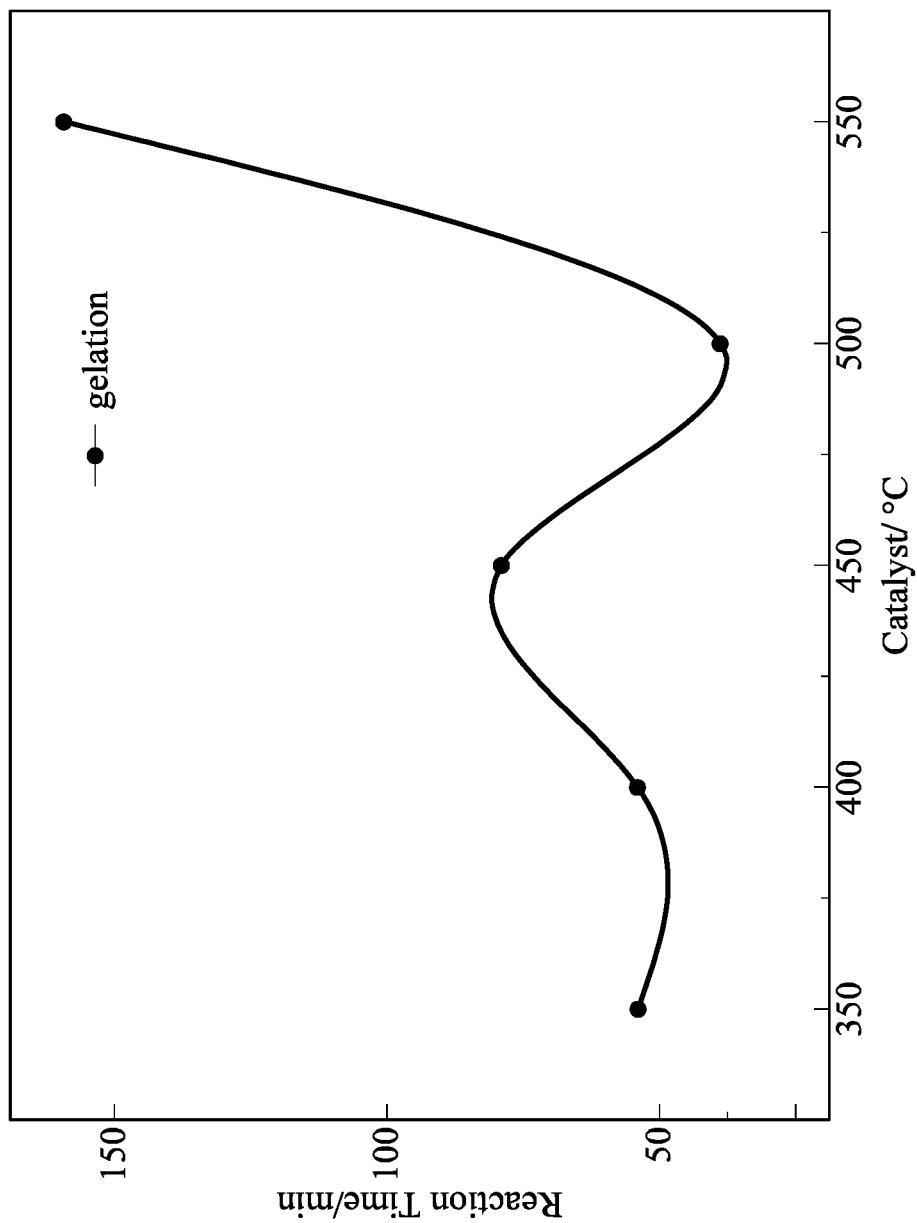

Reference is now made to FIGS. 7 and 8 which show esterification reactions between sebacic acid and glycerol in a molar ratio of 1:1 and 1:2 respectively. As shown in FIG. 7, in the case of reacting sebacic acid with glycerol in a molar ratio of 1:1, the gelation time of the PGS polymer based on the sulfated titania catalyst that is prepared by the aforesaid wet impregnating method can be reduced to less than about 90 minutes from several hours. As shown in FIG. 8, in the case of reacting sebacic acid and glycerol in a molar ratio of 1:2, the gelation time of the PGS polymer based on the sulfated titania that is prepared by the aforesaid wet impregnating method can be reduced to less than about 150 minutes from several hours. It is worth mentioning that the 500° C. calcined sulfated titania catalyst catalyst is an optimized superacid catalyst for the two esterification reactions.

In the step S104, the semi-finished products formed in the step S102 are molded with a crosslinking agent to form a final product. The final product has excellent mechanical properties (e.g., tensile strength), wear resistance, solvent resistance, weather resistance, and gas tightness. In practice, any suitable molding mean well known in the art can be used to mold the semi-finished products.

One of the advantages of the instant disclosure is that the method use a sulfated titania catalyst to promote the esterification reaction between acid alcohol components, preferably between a specific diacid and glycerol, such that the reaction time can be reduced significantly and the polyester elastomer (i.e., PGS polymer) produced has excellent biocompatibility and biodegradability and good mechanical properties. The evidences regarding the result of the reaction time reduction are shown below.

Based on the above, the method can meet the requirements of large-scale production, and the polyester elastomer can be widely used in biomedical fields as well as industrial fields.

In addition, the solid superacid catalyst can be recovered from the prepolymer for reuse, such that the method improves environmental and economic benefits.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A method for preparing a biodegradable polyester elastomer, comprising:
    dissolving titanium dioxide in an aqueous mixture of sulphuric acid, DI water, and ethanol to form a first solution;
    refluxing the first solution at a temperature of 90-100° C. to form a second solution, wherein the first solution is refluxed in a silicone oil bath with a stirring speed of 300-450 rpm;
    drying the second solution to form a catalyst raw material, the second solution being dried at a temperature of 90-120° C.;
    grinding the catalyst raw material and calcining resulting particles at a temperature of 350-550° C. to form sulfated titania as a solid superacid catalyst; and
    carrying out an esterification reaction between one of maleic acid and adipic acid and glycerol in a molar ratio of 1:1-2 with an effective amount of the sulfated titania under a vacuum pressure of 300-600 mTorr to produce a prepolymer, wherein the effective amount of the sulfated titania is at least 1.5-2 mol % based on the diacid and glycerol.

2. The method according to claim 1, wherein the sulfated titania is a 500° C. calcined sulfated titania catalyst.

3. The method according to claim 1, wherein the esterification reaction is carried out at a temperature of 25-150° C.

4. The method according to claim 3, wherein the esterification reaction is carried out at 130-150° C.

5. The method according to claim 1, wherein the esterification reaction is carried out with a stirring speed of 300-400 rpm.

* * * * *